United States Patent [19]

Abrevaya et al.

[11] Patent Number: 4,714,692

[45] Date of Patent: Dec. 22, 1987

[54] MICROEMULSION IMPREGNATED CATALYST COMPOSITE AND USE THEREOF IN A SYNTHESIS GAS CONVERSION PROCESS

[75] Inventors: Hayim Abrevaya, Chicago; William M. Targos, Palatine, both of Ill.

[73] Assignee: UOP Inc., Des Plaines, Ill.

[21] Appl. No.: 847,981

[22] Filed: Apr. 3, 1986

[51] Int. Cl.$^4$ .................... B01J 23/46; B01J 37/02
[52] U.S. Cl. .................... 502/261; 252/313.1; 502/263; 502/300; 502/325; 502/332; 502/523; 518/715
[58] Field of Search ............... 502/332, 325, 261, 185, 502/263, 300

[56] References Cited

U.S. PATENT DOCUMENTS

| | | | |
|---|---|---|---|
| 3,897,368 | 7/1975 | Ohara et al. | 502/332 |
| 4,042,614 | 8/1977 | Vannice et al. | 502/185 |
| 4,171,320 | 10/1979 | Vannice et al. | 502/332 |
| 4,425,261 | 1/1984 | Stenius et al. | 502/339 |
| 4,495,306 | 1/1985 | Budahn et al. | 502/185 |

FOREIGN PATENT DOCUMENTS

| | | | |
|---|---|---|---|
| 0011476 | 5/1980 | European Pat. Off. | 502/261 |
| 1175148 | 12/1969 | United Kingdom | 592/332 |

OTHER PUBLICATIONS

M. Boudart, J. Phys. Chem., vol. 88 (11), 1984.
H. Nijs et al., J. Chem. Soc. Chem. Com., p. 180, 1979.
Hugues et al., New Horizons in Catalysis, Kodansha Ltd., Tokyo, p. 418, 1981.
Vanhove et al., J.C.S. Chem. Comm., p. 605, 1979.

Primary Examiner—Paul E. Konopka
Attorney, Agent, or Firm—Thomas K. McBride; John F. Spears, Jr.

[57] ABSTRACT

A catalyst composition for synthesis gas conversion comprising a ruthenium metal component deposited on a support carrier wherein the average metal particle size is less than about 100 A. The method of manufacture of the composition via a reverse micelle impregnation technique and the use of the composition in a Fischer-Tropsch conversion process is also disclosed.

6 Claims, No Drawings

MICROEMULSION IMPREGNATED CATALYST COMPOSITE AND USE THEREOF IN A SYNTHESIS GAS CONVERSION PROCESS

The Government of the United States of America has rights in this invention pursuant to Contract No. DE-AC22-84PC70023 awarded by the U.S. Department of Energy.

BACKGROUND OF THE INVENTION

This invention relates to catalytic compositions of matter having a specified metal particle size range deposited thereon and their methods of manufacture. In addition, this invention relates to a process for the catalytic conversion of a synthetic feedstock to hydrocarbonaceous materials by contacing said feedstock with a catalytic composite comprising metal particles deposited thereon in a specific size range.

The size of a metal particle on a support may be very important to developing a catalyst which meets the activity, stability and selectivity requirements of a particular catalytic process. For example, it has been noted that synthesis gas conversion may be improved by controlling the particle size of the active metal on a catalytic support. M. Boudart, *J. Phys. Chem.*, v. 88, (11), 1984. A means for controlling the size of metal particles to be impregnated is through the employment of microemulsions. The term "microemulsions" has been used to describe a variety of multi-component systems. In the instant invention a microemulsion is defined as a thermodynamically stable solution of water, hydrocarbon and surfactant which has the property of transmitting light equally in all directions. The microemulsions contemplated by the present invention are systems in which the hydrocarbon forms a solvent containing water in a reverse micelle, i.e., water pools surrounded by surfactant molecules. Each reverse micelle contains one water pool which may be thought of as an aqueous nuclei or water core. The water cores are isolated from one another by the nonaqueous environment.

The prior art discloses that metal salts may be dissolved into the individual water pools of the microemulsion. For example, in U.S. Pat. No. 4,425,261 reverse micelle microemulsions comprising hexane, pentaethylene glycol dodecylether (PEGDE), water, and respectively platinum, palladium, and rhodium salts were prepared. The metal compounds employed were dissolved and encapsulated in the water core of the reverse micelle. In order to obtain an impregnant of uniform metal particles, the micelle solution was first neutralized with an alkali base such as sodium hydroxide and the metal in the water core of the micelle was subsequently reduced with a reducing agent such as hydrogen and/or hydrazine. The metal particles formed in this way were uniform in size and did not deviate more than $\pm 10\%$ in diameter. Only after the metal particles were reduced and metal flakes were formed within the water core could the metals be deposited on an oxide support. In other words, the impregnant disclosed by patentee necessarily requires the active impregnate metal to be present in a reduced valence state prior to contact with any oxide support.

The above described liquid suspension is believed to be the closest prior art disclosing reverse micelle containing impregnant solutions. Although patentee's liquid suspension is functional, it is not readily adaptable to commercial catalyst manufacture. First, the preparation of patentee's liquid suspension requires multiple steps leading to high economic inefficiency. For example, the reuse of starting materials and reagents, a common manufacturing technique, may be inhibited. Also, the impregnation of reduced metal particles on an oxide support does not generally result in an acceptable catalyst because the requisite thermal stability cannot be achieved. The transfer of colloidal metallic particles onto a support surface lacks sufficient metal-support chemical interaction, a feature which is generally accepted as a requisite for good catalytic action. Desirable metal-support interaction is gained usually when the metallic state is achieved in the presence of the support during catalyst finishing. In addition, the colloidal metallic particles in the patentee's description may also agglomerate during impregnation or transfer onto the surface of a support, leading to broad metallic size distribution.

The catalyst composition contemplated in the present invention is prepared from an impregnant medium which avoids these problems by maintaining the metal impregnate ions contained in the water core of the reverse micelle in a nonreduced state. In accordance with the process for catalyst manufacture employing the reverse micelle containing liquid impregnant medium of the present invention and in contradistinction to the prior art, the metal ions contained in the water cores of the impregnant solution are reduced directly on the support surface after impregnation of the micelle.

There are a number of recent reports in the literature concerning selective synthesis of hydrocarbons via certain Fischer-Tropsch type catalysts. For example, deviations from ASF distribution have been obtained by employing rethenium particles having narrow size distributions and encaged in Y-faujasites. See Nijs et al, *J. Chemical Society Chemical Communications*, page 180 (1979). Thus, a hydrocarbon product distribution was obtained with cutoffs at $C_3$, $C_5$ and $C_{11}$ with 13 A, 20 A and 40 A Y-zeolite encaged ruthenium, respectively. It was reported that these deviations were due to the catalyst geometry imposing a size on the ruthenium particles. Similar deviations from ASF distribution have also been obtained with alumina supported, carbonyl derived iron particles. See Hughes et al, *New Horizons in Catalysis*, Kodansha Ltd., Tokyo, page 418, 1981. For these catalysts a cutoff carbon number of 4 was obtained with a very high selectivity at $C_2$. With time, however, these particles sintered and lost their selectivity to light hydrocarbons. Finally, it has also been observed that the pore size distribution of a support may influence selectivity possibly by limiting the size of the active metal particle. See Vanhove et al, *J. Chemical Society Chemical Communications*, page 605, 1975. The results obtained with cobalt/alumina catalysts indicate that when the average pore diameter of the support was increased from 65 A to 300 A, the product distribution shifted towards nigher hydrocarbons: from $C_3$-$C_{10}$ to $C_{14}$-$C_{20}$.

Thus, evidence suggests that Fischer-Tropsch is a structure sensitive reaction and that selectivity is related to metal particle size.

The object of this invention therefore is to provide a catalytic composition of matter having a specified metal particle size range deposited thereon and its method of manufacture. Further, it is an object of the present invention to provide for a method of impregnating uniform Group VIII metal crystallites on a support material. In addition, it is also an object of the present invention to provide for an improved process for the conversion of synthesis gas comprising carbon monoxide and hydrogen to hydrocarbonaceous materials. Finally, it is also an object of the present invention to effect desired selectivity in the synthesis of hydrocarbons by controlling the geometry of the catalysts employed, in particular, the size of the metal particles deposited on the catalytic support. Further objects and embodiments of the present invention will become apparent to those skilled in the art and are intended to be included within the scope of the present invention.

SUMMARY OF THE INVENTION

As provided herein, the present invention provides for a catalytic composition comprising metals deposited thereon in a particular particle size range for the use in the synthesis conversion to hydrocarbonaceous materials. Furthermore, there is provided a process for the catalytic conversion of a feedstock comprising hydrogen and carbon monoxide to hydrocarbonaceous materials which comprises contacting said feedstock at conversion conditions with a catalytic composition comprising a platinum group metal deposited on a refractory inorganic oxide support wherein the average metal particle size is 100 A. Further embodiments of the present invention which are obvious to those skilled in the art or disclose herein are also contemplated.

DETAILED DESCRIPTION OF THE INVENTION

Microemulsions are thermodynamically stable and optically isotropic solutions of water, hydrocarbons and at least one surfactant. The microemulsion system contemplated by the present invention is a system known as a reverse micelle. In the reverse micelle a water core or nuclei is surrounded by the polar head groups of the surfactant. The nonpolar portion of the surfactant extends into the nonpolar hydrocarbon solvent solution thus forming the reverse micelle. When metals are dissolved in the water used in the preparation of the reverse micelle, the metals become encapsulated in the water core. The individual water cores which make up the reverse micelle solution are isolated from one another by the nonaqueous environment. An important factor which contributes to the size of a metal particle which is ultimately deposited on a support material from the reverse micelle containing impregnant solution is the amount of water present in each individual microemulsion. Even though the precise structure of reverse micelles is still not known, the size and shape of these microemulsions are dependent on the surfactant, solvent, the amount of water and metals dissolved therein.

Without being limited to theory, it is postulated that the size of the water core of a reverse micelle plays a role in producing a suitable impregnant medium. Very small amounts of water are preferred in the present invention. Even though amounts as high as 5 wt. % may be employed, it is preferred by the present invention that the water be present in amounts less than 4.0 wt. %, more preferably less than 3.0 wt. %. The amount of water present affects the size of the water core as measured by the volume average water core diameter. Preferably the size of the water core is in the range of about 10 to 200 A and more preferably in the smaller size range of about 20 to 90 A.

The surfactant employed in the present invention will possess both polar and nonpolar characteristics. The polar head groups of the surfactant occupy the interior of the reverse micelle while the hydrophobic hydrocarbon charge of the surfactant extends into the nonpolar solvent. In a reverse micelle, the polar phase may or may not contain water. In the present invention, however, the polar phase contains water in the core of the reverse micelle and may be generally referred to as a water in oil (w/o) dispersion. The surfactant may be a nonionic, ionic or cationic compound. Polyethylene dodecyl glycol ethers are preferred nonionic surfactant compounds. Even though the number of carbon atoms in the carbon chain are not particularly critical, nonionic surfactants comprising about 10 to 16 carbon atoms in the carbon chain are preferred. Thus, for example, a particularly preferable surfactant is polyethylene glycol dodecyl ether. Suitable anionic surfactant compounds include sodium dodecyl sulfate. Suitable cationic surfactant compounds include cetyl trimethyl ammonium halides. A particularly preferred cationic surfactant is cetyl trimethyl ammonium bromide. Suitable co-surfactants include medium chain length alcohols such as n-octanol. Other suitable surfactants include butanol.

The surfactant may be present in the impregnant solution in a concentration range of 5 to 40 wt. %. Preferably, the surfactant is present in a concentration range of 15 to 26 wt. %. The surfactant should also be present in a weight ratio range of surfactant to water of about 0.2:1 to 40:1. More preferably, the weight ratio range will be from 6:1 to 24:1. The above concentration and weight ratio ranges are most preferred when a nonionic surfactant is employed. Co-surfactants, i.e., combinations of one or more nonionic, anionic, and/or cationic compounds are also contemplated by the present invention. Thus, reverse micelle impregnant solutions comprising co-surfactants such as n-butanol and pentaethylene glycol dodecyl ether are contemplated by the present invention.

The hydrocarbon solvent employed in the present invention should not have any chemical reactivity with other components of the solution. The hydrocarbon should also have a substantially nonpolar characteristic so that the nonpolar portion of the surfactant is readily soluble therein, while water, which forms the water core of the formed reverse micelle is substantially insoluble in the hydrocarbon. Hydrocarbons which are useful as solvents for the instant impregnant solution comprise aliphatic noncyclic hydrocarbons such as hexane, heptane, octane, etc., and their branched isomers. Also, aliphatic cyclic hydrocarbons are contemplated by the present invention. Since the reverse micelles of the impregnant solution are ultimately impregnated on a carrier, it is preferred that the hydrocarbon solvent is readily volatile under finishing conditions. Thus, hydrocarbon solvents in the 6 to 10 carbon atom range will possess the generally preferred volatility characteristics.

The selection of a metal compound is critical to the instant impregnant solution. In order to be effective as an impregnant medium, a high metal concentration in the water core is necessary. If the metals content is too low, the resulting aggregate amount of metal deposited on a support carrier by way of the impregnant medium will be too small to effect any substantial catalytic activity in a conversion process. In addition, since the concentration of water in the impregnant solution is very low and therefore the size of the water core is very small a high metal solubility is contemplated. Moreover, a small water core diameter enhances the control of the size of metal particles deposited on a carrier, while more metal can be deposited. Thus, in order to obtain a sufficient catalytic amount of metal on a particular carrier, a high concentration of the metal compound in the water core is necessary. Metal ion concentrations in the water core of the reverse micelles is preferably greater than 0.1 mole per liter. More preferably, when a catalytic amount of at least 1 wt. % metal is required to be deposited on a carrier, the metal ion concentration in the water core should be at least 0.5 mole per liter. Most preferably, the metal ion concentration in the water core is in the range of about 0.5 to 2.5 moles per liter. Metal compounds which are suitable for the present invention include the metal salts and acids. Thus, chloro metal acids as well as the metal chlorides are contemplated. In cases where its formation is possible, a most preferred compound, due to its high solubility, is the metal nitrosyl chloride. Thus, in the case of platinum, chloroplatinic acid or its sodium salt are contemplated. Likewise, similar compounds for other Group VIII and platinum metals, such as palladium, rhodium, osmium, ruthenium, iridium, iron, nickel, and cobalt are contemplated. Because of its high water solubility, a particularly preferred ruthenium compound is ruthenium nitrosyl chloride.

It is also contemplated by the present invention that the aqueous solution may be modified by any manner known to those skilled in the art to increase the metal solubility. Thus, increasing metal solubility through lowering the pH of the aqueous solution by adding concentrated hydrochloric acid, aqua regia ($HCl/HNO_3$), etc., to allow a greater amount of metals to be dissolved therein in contemplated by the present invention. For example, if the compound chloroplatinic acid were the metal precursor, and a high platinum metal content were desired, concentrated hydrochloric acid may be added to water in an amount sufficient to achieve the desired platinum concentration. Thus, although a metal compound with high solubility is preferred, solvent modification such as that described above (or similar techniques increasing metal solubility) are contemplated by the present invention in order that a high metals concentration in the water core is achieved.

Even though at the present time the Group VIII metals such as ruthenium, platinum, iron, cobalt, nickel, palladium, rhodium, iridium, and osmium are preferred, other metals are contemplated by the present invention. Thus, metals of Group IA, IIA, IIIB, IVB, VB, VIB, VIIB, IB, IIB, IIIA, IVA, VA and those of the Lanthanum series, as well as any combination thereof, are also contemplated. Specifically contemplated metals include potassium, lithium, cesium, rubidium, magnesium, titanium, zirconium, vanadium, chromium, molybdenum, tungsten, silver, gallium, indium, germanium, tin, antimony, cerium, and any combination thereof. Also contemplated are compounds of the above metals which will dissolve in an aqueous solution in sufficient amounts to achieve the high metal concentrations contemplated by the present invention in the reverse micelle water core.

Two mutually insoluble phases such as water and oil can be made to disperse within each other by means of a surfactant which lowers the interfacial tension between them. An oil in water, o/w (normal), or a water in oil, w/o (reverse), micelle system is formed, depending upon whether the surfactant-water or the surfactant-oil interfacial energy is lowered to a greater extent.

The overall micelle formation process is favorable also because the entropy change for dispersing the oil and water phases is positive.

Kinetics of micellization is fast, i.e., the time constant of the slowest step usually being in the order of milliseconds. Thus, a narrow micelle size distribution around a thermodynamically determined value is quickly achieved upon mixing of the oil/surfactant/water mixture.

Although the relative contribution of factors affecting micelle formation and the final equilibrium state of the micelle system is not well understood, micelle size can be controlled with the choice of the proper parameters. A co-surfactant, such as a medium chain length alcohol, can be added to the oil+water+surfactant mixture to lower the interfacial tension between the insoluble phases to an even greater extent and therefore allow a further decrease in micelle size. Suitable cosurfactants contemplated comprise compounds selected from the straight chain aliphatic alcohols. Preferably, the alcohols comprise from about 3 to 6 carbon atoms. Thus, propanol, butanol, pentanol and hexanol are preferred. However, the co-surfactant, which is usually more hydrophobic than the surfactant, can position itself between the surfactant molecules and cause an increase in the average distance between the polar head groups. This would decrease the electrostatic repulsive forces, and possibly cause micelle growth by agglomeration. An electrolyte like NaCl has a similar effect by supplying counterions to the polar head groups of the surfactant. The equilibrium size of an o/w (normal) micelle will, for instance, increase with the extent of the oil phase. Water has a similar effect on the size of w/o reverse micelles. Temperature, particularly for nonionic surfactants, can also be used to vary the micelle size.

The reverse micelle impregnant solution may be prepared by first dissolving the metal compounds in water to form a metal ion solution. The water metal ion solution is subsequently admixed with a previously prepared admixture of surfactant and hydrocarbon solvent. The two solutions are admixed to form the impregnant medium which is a clear solution containing the reverse micelle.

The impregnant medium of the present invention is used to impregnate the metals dissolved in the water core of the reverse micelle onto a particular support carrier. Carrier materials include any refractory inorganic oxide, amorphous or crystalline, which have pores large enough for penetration of reverse micelles. For examples, carriers such as alumina, silica, silica alumina, titania, magnesia, and other known metal oxide supports are contemplated.

Catalyst compositions may be manufactured by impregnation techniques known in the art. Well known methods such as dip and vacuum impregnation are contemplated. In addition, impregnation may be carried out in a single contacting step or multiple steps with reverse micelle containing solutions which contain identical or different metals. Moreover, impregnation by a reverse micelle containing impregnant solution followed by a conventional impregnant solution or vice versa for the impregnation of a support is also contemplated.

Also contemplated by the present invention is the preparation of catalyst compositions comprising more than one specified range of metal particles impregnated on a support material. Thus, metal size combinations of, for example, 5-10 A, 10-20 A, 40-60 A, 20-40 A, 80–100 A, etc., are contemplated. Such multi-range metal particle containing catalysts may be formed by multi-step impregnation techniques known to those skilled in the art. The particular method of impregnating two different metal particle sizes on the same support material is not considered to be a limitation of the present invention.

A preferred impregnation procedure comprises contacting a support material (ground powder, spherical beads, pellets, extrudates, preferably 40–200 mesh powder) with the impregnant solution and agitating the admixture. In the cases where platinum and/or palladium metal ions were dissolved in the reverse micelle water core, the impregnant solution turned colorless while the support material took on a light yellow shade. It is believed that the time for which the support material is contacted with the impregnant solution may be important when a high degree of metal uptake is required. For example, in preparing catalyst batches of 50 grams to 100 grams in size, it was found that the support and impregnant solution should be brought into contact over a period of about ½ to 1 hour in order to obtain 1 wt. % of metal on the carrier. After impregnation, the remaining liquid is decanted and the impregnated support is recovered and air dried. After air drying, organic compounds which have remained on the impregnated support may be removed by a helium purge at about 50°–300° C. The helium purge is presently contemplated to be optional depending upon the metal which is being deposited. Residual organics and carbonaceous deposits on the impregnated support may also be removed by air oxidation at a temperature sufficiently high to cause removal of the organics from the support but not so high as to cause metal particle agglomeration. The calcination temperatures preferably range between about 200° C. to 500° C. For example, in the case of ruthenium, the calcination temperature must be between about 250° C. and 380° C. and preferably is about 300° C.±20° C. since temperatures less than 250° C. are insufficient to effectively remove the organics present and temperatures greater than 380° C. will cause substantial metal agglomeration. The metal crystallites impregnated on the support, are then reduced while on the support surface by contact with flowing hydrogen at about 200°–500° C. The oxidation step may be carried out in a fixed or fluidized bed, the latter being more preferable when larger batches of catalyst are to be manufactured.. The metal compounds on the support are reduced while on the support surface by contact with flowing hydrogen.

Catalyst compositions prepared according to the impregnation technique employing a reverse micelle impregnant solution possess a uniform size range of metal particles. The upper and lower limits of a particular metal particle size range may differ as little as about 5 A. Preferably, the metal particle size range limits will differ between 10 to 20 A. Minimum particle sizes contemplated are about 5 A. The maximum particle size may be as great as 200 A. Catalyst compositions comprising impregnated metal particle ranges of 5–10 A, 10–20 A, 20–30 A, 20–40 A, 30–40 A, 40–60 A, 60–80 A, 100–120 A, 120–140 A, 140–160 A, 180–200 A, etc. are contemplated. It is believed that the size of the metal particles impregnated on the support are dependent upon the particular combination of the size of the water core of the reverse micelle and the concentration of the size of the metal within the water core..

A unique characteristic of the catalysts prepared by the present technique is that substantially all of the active metal impregnated on the support is found as metal particles in a pre-specified metal particle size range. By the term "substantially," it is meant that at least 90 wt. % of the impregnated metal as detected by state of the art analytic methods is impregnated on the support as clusters of metal particles within the pre-specified range. Preferably, 95 wt. % of the impregnated metal will be present as clusters of metal particles within the pre-specified metal particle size range.

The catalyst compositions of the present invention also comprise amounts of active metals sufficient to impart a catalytic effect when impregnated on a support. Weight percentages between 0.1 wt. % and 20 wt. % of the total catalyst composition are contemplated. The uniqueness of the instant catalyst compositions is attributed to the ability to dissolve large amounts of metal ions into the small water core of the reverse micelle contained in the impregnant medium. Thus, the unique properties of the present catalyst compositions are, in part, accredited to the high solubility of the particular metal compound chosen for preparation of the reverse micelle impregnant solution. In addition, without being limited to theory, it is believed that the minimization of the water core size discourages agglomeration of the metal particles during impregnation. The exact relationship, however, between the metal compound solubility and water core concentration, water core size and impregnation technique, are not completely understood. It is to be noted that stability of the metal particles as against agglomeration may be dependent on a number of parameters in addition to those mentioned including calcination conditions, support size and the severity of the conditions of any process in which the catalyst is employed.

In any event, the present invention allows for the design and construction of catalyst compositions having pre-determined and pre-specified metal particle size ranges impregnated thereon. The instant novel catalyst are advantageous over prior art colloidal metal containing catalysts in that the stability, as against metal particle agglomeration, is much greater. It is believed that the higher stability of the instant catalyst results from the particular chemical interaction between the impregnated metal particles and the support. The exact bonding between the impregnated metal and oxide support is not known, but is is postulated that a highly integrated bonding network which is formed by way of air oxidation and then reduction of the metal ion while impregnated on the support contribute to this unique agglomeration stability.

The present invention is useful in catalytic processes which are known to be effected by the metal particle size of a particular catalytically active metal component on a catalytic support. One particular process in which the catalyst of the present invention may be employed is the selective conversion of synthesis gas into hydrocarbon fuels (especially transportation fuels).

The enormous reserve of coal deposits in the United States represents a major potential source of liquid transportation fuels. The two general approaches for transforming solid coal into liquid products are direct and indirect liquefaction. Direct coal liquefaction processes generally use hydrogen addition to directly produce a liquid product which must then be substantially refined in order to provide transportation quality fuels. Indirect techniques generally convert coal into a gaseous mixture containing mainly hydrogen and carbon monoxide. This mixture (synthesis gas) can be catalytically converted into a high quality hydrocarbon mixture which can readily be used to make transportation fuels.

The present invention provides a process which will substantially improve the indirect liquefaction of coal into transportation fuels. The selectivity for conversion of coal derived synthesis gas into transportation fuels with current catalytic systems is limited by the Anderson-Schulz-Flory polymerization law, which describes the broad range of products obtained. Enhanced production of specifically desired fuels such as gasoline, jet fuel and diesel fuel would provide a significant advance in the commercialization of technologies to produce fuels based on indirect liquefaction of coal.

Recent work indicates that the molecular weight of synthesis gas conversion products is limited by the size of the metallic particles serving as catalysts. Specifically, the particle size can be used to provide a cut-off for the upper end of the product distribution and therefore provide substantial deviation from the Anderson-Schulz-Flory polymerization law; the higher the chain growth probability is prior to cut-off, the more dramatic the deviations. However, this concept of improving selectivity by controlling catalyst geometry has not yet resulted in a breakthrough.

The present invention provides for an improved synthesis gas conversion process by employing a novel catalyst comprising supported metal particles of specific and well defined sizes. The support material employed may be any refractory inorganic oxide material with large enough pores for reverse micelles to penetrate such as silica, alumina, silica-alumina, titania, magnesia, zinc or any similar metal oxide. Preferably, the support material is alumina.

The active metal component impregnated on the catalyst support shall be selected from the Group VIII or platinum group of metals. The preferable metal component is ruthenium. The specific size range of the metal particles on the support is greater than 20 A but less than 60 A. Preferably, the metal particles will be present in the size range of 40 A to 60 A. The active metal must be present in a catalytically effective amount. In the instant synthesis gas conversion process, the active metal is preferably present in an amount between 0.1 wt. % and 10 wt. %. More preferably, the active metal is present on the support in an amount between 0.5 wt. % and 5 wt. %.

In order to obtain the preferred metal particle size range of 40 A to 60 A on the support, the preferred method of impregnation is the reverse-micelle technique. Although this technique is not deemed essential to the present invention, it is the best impregnation method contemplated.

As above stated, the feed stocks in the synthesis conversion process comprise hydrogen and carbon monoxide. The feedstocks may be derived from a number of synthetic processes such as coal gasification. In any event, the feedstock is to comprise hydrogen and carbon monoxide in a molar ratio range of about 0.4 to 3.0 and preferably in the range of about 0.5 to 0.9.

The synthetic conversion conditions include a temperature range of about 300° F. to about 700° F. and a pressure range of about 0 psig to 3000 psig. In addition a gas hourly space velocity (GHSV) of about 50 to 2000 hr.$^{-1}$ is also contemplated.

It has also been observed that low temperature water gas shift selectivity with ruthenium increased with a decrease in ruthenium particle size. This phenomenon suggests that a catalyst comprising the particular combination of a predetermined ruthenium particle size such as 40–60 A and highly dispersed ruthenium particles (i.e., less than about 10 A) will not only allow for the production of less light ends in a synthesis gas conversion process but also optimize hydrogen to carbon monoxide feed ratios.

In addition to synthesis gas conversion, other processes contemplated by the present invention include reforming, hydrogenation, hydrocracking, catalytic cracking, paraffin dehydrogenation, and emission control.

The examples below are merely exemplary of the present invention and are not intended to limit the scope of the appended claims. Modifications, additions, and alterations to the impregnant medium exemplified below which are obvious to those skilled in the pertinent art area are also contemplated herein and are not outside the spirit of the present invention.

EXAMPLE 1

The reverse micelle technique was employed to prepare various specific size ruthenium particles supported on gamma alumina while maintaining the same total amount of ruthenium on the catalyst. The specific ruthenium particle size depends on the reverse micelle water core size and the ruthenium concentration in the water core.

Two catalysts containing approximately 1 wt. % total ruthenium were prepared by the reverse micelle technique. Catalyst A was prepared with a ruthenium metal particle size range of 20–40 A, Catalyst B was prepared with ruthenium metal particles having the size range of 40–60 A. The third catalyst (Catalyst C) was prepared by a conventional impregnation technique known in the art. Catalyst C had a high dispersion of ruthenium particles wherein the particles were much less than 20 A in size. Catalyst D was prepared such that after analytical examination it was found to have a broad ruthenium metal particle size range of 40 A to 2000 A.

Catalysts A and B were prepared from reverse micelle impregnant solutions. The reverse micelle impregnant solutions were prepared by mixing a pentaethylene glycol dodecyl ether (PEDGE) surfactant with n-hexane solvent and a ruthenium solution containing 0.5 molar ruthenium. The specific ruthenium particle size ranges of Catalysts A and B were achieved by contacting an alumina support with two different reverse micelle impregnant solutions 1 and 2 which were prepared as below:

| REVERSE MICELLE IMPREGNANT SOLUTIONS AND CATALYSTS | | |
|---|---|---|
| Solution No. | 1 | 2 |
| PEGDE (g) | 36 | 144 |
| n-hexane (g) | 197.7 | 395.4 |
| Ru. Soln (g) | 6 | 6 |
| Ru Conc. in Water Core, molar | 0.5 | 0.5 |
| Amount of alumina (g) | 30 | 30 |
| Water Core Radius, A | 11 | 38–45 |
| Corresponding Catalyst | A | B |
| Ru Particle Size Range A | 20–40 | 40–60 |

Catalysts A, B, C and D were compared in a fixed bed pilot plant for synthesis gas conversion catalytic performance. In each experiment a Co/H$_2$/Ar feed system was employed. A H$_2$/CO feed ratio of 0.9 was passed downflow through a 30 cm long 1 cm inner diameter stainless steel reactor, first through a 10 cm long quartz chips preheater section, followed by a 10 cm long catalyst bed. A thermowell passed through the center of the reactor. The reactor was in an electric furnace. The effluent from the reactor was passed through a series of product collectors at different temperatures (110° C., 0° C. and −78° C.) and then metered by a wet test meter. CO, H$_2$, CO$_2$, CH$_4$ and Ar at the reactor exit were monitored by on-line gas chromatography. Argon was used as an internal standard to measure the conversion of CO. The effluent gas was also analyzed by off-line gas chromatography to determine the concentration of CO, CO$_2$, H$_2$, Ar, CH$_4$, C$_2$–C$_5$ paraffins and olefins. Each test was conducted for about 200 hours. The respective used catalysts were treated with toluene, after each run, to extract the wax that had deposited. The carbon on the used catalysts was then determined by a combustion technique. The products collected during the run were separated into an aqueous and an organic phase. The aqueous phase was analyzed by gas chromatography to determine the concentration of H$_2$O and C$_1$–C$_4$ alcohols. The organic phase was analyzed by boiling point analysis to determine the concentration of C$_2$–C$_{60}$ hydrocarbons. Higher molecular weight hydrocarbons were analyzed by gel permeation chromatography.

The data in Table I was collected by a number of analytical techniques. The state and amount of ruthenium was analyzed on both fresh and spent catalysts by scanning transmission electron microscopy, hydrogen uptake and atomic absorption spectroscopy. The amount of hydrocarbon produced is reported in grams of hydrocarbon per hr-gm ruthenium in the fresh catalyst. The moles of ruthenium exposed is reported in moles Ru per gram of catalyst and was measured by hydrogen uptake assuming every ruthenium atom takes up one H$_2$ molecule. The turnover number which is indicative of catalytic performance is reported in moles of carbon atom converted per sec-mole Ru atom exposed. Finally, the size range of ruthenium particles on fresh and spent catalysts as measured by scanning transmission electron microscopy (STEM), is reported in angstroms, A.

TABLE I

COMPARISON OF CATALYSTS OF VARIOUS RUTHENIUM PARTICLE SIZE

| Catalyst | A | B | C | D |
|---|---|---|---|---|
| Ru Content, wt. % | | | | |
| Fresh | 0.86 | 0.93 | 1.09 | 1.1 |
| Spent | 0.37 | 0.96 | 0.62 | 1 |
| Hours of test | 220 | 248 | 152 | 81 |
| HCBN Produced g/hr-g ruthenium | 0.74 | 1.4 | 0.42 | 0.75 |
| Ru exposed[a] (mole/g cat) × 10$^6$ | 28 | 12 | 86 | — |
| Ru disper. wt. %[b] | 33 | 13 | 91 | — |
| Turnover Number × 10$^3$[c] | 4.6 | 21 | 1.1 | Very low |
| Ru Particle Size, A | | | | |
| Fresh | 20–40 | 40–60 | <20 | 40–2000 |
| Spent | 100–300 | 40–60 | 200–1000 | 40–2000 |

[a]measured by H$_2$ uptake assuming every Ru atom takes up 1 h$_2$ molecule.
[b]Ru exposed/(moles Ru/g catalyst).
[c]mole C converted/sec-mole Ru exposed.

The data collected in Table I reveal that Catalysts A and B which have specific ruthenium particle size ranges have substantially high turnover numbers in comparison to Catalysts C and D. High turnover numbers are indicative of better catalyst performance and higher synthesis gas conversion activity. Moreover, Catalyst B, as indicated by the lack of agglomeration of ruthenium particles on the spent catalyst, is considered to be more stable than Catalyst A.

EXAMPLE II

Catalyst B of Example I was compared against a standard iron reference catalyst (Catalyst E) which was obtained from United Catalyst Inc. (C-73-101). Synthesis gas feed was passed through the pilot plant described in Example I and contacted with Catalyst B and Catalyst E, respectively at 208° C. and 35 atm. The product distributions obtained in these two tests are given in Table II. The same Table II also shows results obtained with a state of the art iron-containing precipitated catalyst (Catalyst F) which is identical to that employed in the Sasol Arge (South Africa) reactor at 220° C. and 27 atm. The data shows substantially less selectivity to light end products (C$_1$–C$_4$) by Catalyst B than by the Fe catalysts E and F. Light ends usually are not desirable products of synthesis gas conversion since they are much harder to upgrade to transportation range fuels relative to heavier hydrocarbons. This greater overall selectivity to heavier products with Catalyst B indicates that transportation fuels may be obtained more effectively when the catalyst of the present invention is employed.

TABLE II

SYNTHESIS GAS CONVERSION

| Product Cut | Catalyst B | Catalyst E | Catalyst F |
|---|---|---|---|
| CH$_4$ | 0.53 | 5.7 | 2.0 |
| C$_2$–C$_4$ | 1.15 | 22.7 | 11.3 |
| C$_5$+ | 98.32 | 71.6 | 86.70 |
| C$_{12}$+ | 92.54 | 32.3 | 68.70 |

EXAMPLE III

The following example illustrates the impregnation of a support material employing the reverse micelle impregnant solution as the impregnant medium. A catalyst comprising ruthenium particles in the range of 20 A to 40 A impregnated on alumina was prepared.

The reverse micelle solution was prepared by mixing 360.0 grams of Berol 050 (pentaethylene glycol dodecyl ether, purified by at least three times by freezing, decanting and then filtering (until visually clear) with 988.5 grams (1500 cc) of n-hexane. The mixture was set aside for 16 to 24 hours and filtered to clarity. 15.0 grams of 150 mg salt/g water ruthenium nitrosyl chloride solution was added to the clear surfactant/n-hexane solution to form the reverse micelle solution. The solution was cloudy at first and clarified within 24 hours. After 24 hours, a small amount of solid residue that formed was filtered from the reverse micelle soltuion. The solution contained ruthenium ions dissolved in the water core which had an average diameter of 22 A.

The reverse micelle solution was then contacted with 75 grams of an alumina support previously crushed to 60–100 mesh and dried at 500° C. for 2 hours by contacting steady streams emanating from individual separatory funnels into a single beaker over a period of about ½ hour. The beaker was constantly stirred throughout the contacting period and was continued to stir for an additional 1.5 hours. The impregnated catalyst was recovered by filtering over a period of about 1 hour. The recovered catalyst was allowed to dry under ambient conditions and then ground to less than 40 mesh size.

The catalyst was then calcined in air (5.9–8.0 SCFH) at an average bed temperature of 450° F.–600° F. (232° C.–315° C.) over a period of 9 hours. After a 4 hour cool down, the catalyst was then reduced in hydrogen (5.0–8.0 SCFH) over a period of 5 hours at an average bed temperature of 932° F.

After cooling, the impregnated alumina support was analyzed and found to contain 0.84 wt. % ruthenium with more than 90% of the ruthenium present in the particle size range of 20–40 A.

What is claimed is:

1. A method for depositing a metal component on a refractory inorganic oxide support carrier whereby said metal component is substantially present as metal particles which are less than about 200 A and do not vary more than 20 A in size which method comprises:

(a) contacting a metal-containing water in hydrocarbon microemulsion liquid impregnant medium comprising aqueous cores containing ions of dissolved unreduced metal therein with said inorganic oxide support carrier under conditions sufficient to fixate said metal-containing aqueous cores to said support;

(b) separating said support from said impregnant medium; and, (c) immobilizing said unreduced metal contained in said aqueous cores by calcining said support in a fluidized bed at temperature conditions sufficient to effect removal of organics from the support but insufficient to effect metal agglomeration on the support and then reducing the calcined support at temperature conditions sufficient to effect metal reduction, but insufficient to effect metal agglomeration on the support.

2. The method of claim 1 characterized in that said calcining temperature conditions are in the range of 200° C. to 500° C. and said reducing temperature conditions are in the range of 200° C. to 500° C.

3. The method of claim 1 characterized in that said metal component comprises ruthenium.

4. The method of claim 3 characterized in that said calcining temperature conditions are in the range of about 250° C. to 380° C.

5. The method of claim 1 further characterized in that said metals are dissolved in said water core at a concentration greater than 0.1 moles per liter.

6. The method of claim 1 further characterized in that said impregnant medium comprises microemulsions having a volume average water core diameter of about 10 to 200 A.

* * * * *